United States Patent [19]

Michejda et al.

[11] Patent Number: 5,808,038
[45] Date of Patent: Sep. 15, 1998

[54] BISTRIAZENES AS CHEMOTHERAPEUTIC AGENTS

[75] Inventors: Christopher J. Michejda, N. Potomac; Jeffrey J. Blumenstein, Germantown, both of Md.

[73] Assignee: The United States of America as represented by the Secretary of the Department of Health and Human Services, Washington, D.C.

[21] Appl. No.: 302,480

[22] Filed: Sep. 12, 1994

Related U.S. Application Data

[63] Continuation of Ser. No. 786,001, Oct. 31, 1991, abandoned, which is a continuation-in-part of Ser. No. 527,915, May 24, 1990, abandoned.

[51] Int. Cl.$^6$ .................... C07C 245/00; A61K 31/655
[52] U.S. Cl. .................... 534/551; 514/150; 514/151; 534/550; 534/552; 534/553; 534/554
[58] Field of Search .................... 534/550–554; 514/151, 150

[56] References Cited

U.S. PATENT DOCUMENTS

| | | | |
|---|---|---|---|
| 2,769,819 | 11/1956 | Sommers et al. | 552/11 |
| 3,187,020 | 6/1965 | Minisci et al. | 552/11 X |
| 3,947,247 | 3/1976 | Kohrman et al. | 8/44 |

FOREIGN PATENT DOCUMENTS

| | | |
|---|---|---|
| 514033 | 3/1953 | Belgium . |
| 0170951 | 2/1986 | European Pat. Off. . |
| 3426644 | 2/1986 | Germany ............... 534/550 |
| 9117753 | 11/1991 | WIPO . |

OTHER PUBLICATIONS

Vaughan et al., Jour. of Medic. Chem. (1984) 27(3):357–403.
Pochinok et al., Chemical Abstracts, (1977) 86(25), #188927k.
Vilenskii et al., Chemical Abstracts, (1967) 67(5), #27572h.
John McMurry, *Organic Chemistry* 2ed., pp. 738–741, 1117–1118 (1988).
John H. Fletcher, et al., Nomenclature of Organic Compounds, p. 167, p. 314 (1974).
G. Zubay, Biochemistry, pp. 664–667 (1983).
B.G. Katzung, ed., *Basic and Clinical Pharmacology*, pp. 668–671 (1987).
P.A.S. Smith, Derivatives of Hydrazine and Other Hydronitrogens Having N—N Bonds, pp. 289–292 (1983).
Clarke et al (1955) Proc. Soc. Exp. Biol. Med. 90:484–88.
R.L. Comis, (1976) Cancer Treatment Reports 60:165–176.
Fiebig et al., (1987) European Journal of Cancer and Clinical Oncology 23:937–948.
Fiebig et al. (1989) Strahlenther. Onkol. 165:522–524.
B.T. Hill, (1987) Cancer Treatment Reviews 14:197–202.
Scalabrino et al. (1981) in Klein et al., eds., Advances in Cancer Research vol. 35, Academic Press, New York, pp. 151–267.
Scalabrino et al., (1982) in Klein et al., eds., Advances in Cancer Research vol. 36, Academic Press, New York, pp. 1–103.
A.E. Pegg, (1988) Cancer Research 48:759–774.
Randall et al. (1984) Journal Chem. Society Perkin Trans. II:251–253.
Schmiedekamp et al., (1988) Journal of Organic Chemistry 53:3433–3436.
Sieh et al. (1981) Journal of the American Chemical Society 103:442–445.
Smith et al., (1984) Journal of the American Chemical Society 106:1056–1059.
Smith et al., (1986) Journal of the American Chemical Society 108:3726–3730.
Smith et al (1988) The Journal of Organic Chemistry 53:1467–1471.
Smith et al., (1986) The Journal of Organic Chemistry 51:3751–3757.
Smith et al. (1989) The Journal of Organic Chemistry 54:1036–1042.
Vaughan et al., (1984) Journal of Medicinal Chemistry 27:357–363.
J.D. Watson (1987) Molecular Biology of the Gene, The Benjamin Cummings Publishing Company, Inc., Menlo Park, California pp. 346–347.
English translation of Pochinok et al., *Ukrain Khim. Zhur.*, 25, 774–780 (1959) "Aliphatic and Aliphatic–Aromatic Bis–Triazenes".
Pochinok et al I, Chemical Abstracts, vol. 54, No. 13034i (1960).
Pochinok et al II, Chemical Abstracts, vol. 86, No. 188927k (1977).
Pochinok et al III, Chemical Abstracts, vol. 102, No. 61876m (1985).
Vilenskii et al, Chemical Abstracts, vol. 67, No. 27572h (1967).
Manning et al, Can. J. Chem., 62(4), pp. 749–754 (1984).

*Primary Examiner*—Floyd D. Higel
*Attorney, Agent, or Firm*—Spencer & Frank

[57] ABSTRACT

The present invention is directed to bistriazene compounds, pharmaceutical compositions containing effective anti-cancer amounts of these compounds, a method for treating cancer comprising administering to affected subjects an anti-cancer effective amount of a bistriazene compound, and the use of bistriazene compounds as crosslinking reagents applicable to the synthesis and manipulation of polymeric macromolecules.

24 Claims, 8 Drawing Sheets

| Lane | Compound | Concentration in mM |
|---|---|---|
| 1 | Control | — |
| 2 | Dimethyltriazene | 5.0 |
| 3 | " | 0.5 |
| 4 | " | 0.05 |
| 5 | 1,2-Bis(methyltriazeno)ethane | 5.0 |
| 6 | " | 0.5 |
| 7 | " | 0.05 |
| 8 | 1,4-Bis(methyltriazeno)-trans-2-butene | 5.0 |
| 9 | " | 0.5 |
| 10 | " | 0.05 |
| 11 | 1,6-Bis(methyltriazeno)hexane | 5.0 |
| 12 | " | 0.5 |
| 13 | " | 0.05 |
| 14 | $\alpha,\alpha'$-Bis(methyltriazeno)-p-xylene | 5.0 |
| 15 | " | 0.5 |
| 16 | " | 0.05 |

BISTRIAZENES AS CHEMOTHERAPEUTIC AGENTS

This application is a continuation of application Ser. No. 07/786,001 filed on Oct. 31, 1991, now abandoned, which was a Continuation-in-Part application of Ser. No. 07/527,915, filed on May 24, 1990, now abandoned.

BACKGROUND OF THE INVENTION

1. Field of the Invention

The present invention relates to the use of bistriazene compounds as chemotherapeutic agents useful in the treatment of various cancers. As such, these compounds find wide utility in both human and veterinary medicine. The invention also relates to the use of these compounds as crosslinking reagents useful in a wide variety of laboratory and chemical applications involving the synthesis and manipulation of polymeric macromolecules.

2. Description of Related Art

A number of chemotherapeutic agents exist which act as alkylating agents capable of forming covalent linkages with a variety of substances, including phosphate groups in DNA. Alkylation of bases in DNA often leads to gene miscoding, serious damage to the DNA molecule, and/or major disruption in nucleic acid function, and results in the inhibition of a wide range of other cellular functions. These agents act by forming lethal crosslinks in nucleic acid molecules, and can often shrink tumors in a matter of days after intravenous administration. Among these compounds are 2-chloroethyl-nitrosoureas such as bis(2-chloroethyl)nitrosourea (BCNU), mitomycin, cyclophosphamide (cytoxan), and ifosphamide. These agents are themselves potentially mutagenic, teratogenic, and carcinogenic, and their anti-neoplastic activity is exerted throughout the cell cycle, i.e., toxicity is cell cycle independent.

Vaughan et al. (1984) *Jour. Med. Chem.* 27:357-63 have reported the formation of a certain bistriazene as a byproduct in the preparation of other triazenes. This bistriazene is chemically and structurally different from those of the present invention, and was not tested for antitumor activity. Furthermore, this bistriazene differs from those of the present invention in that it would require two-fold metabolic activation to release the same alkylating moiety, and is susceptible to hydrolysis, thereby releasing monotriazenes.

The use of the bistriazene compounds of the instant invention as chemotherapeutic and crosslinking agents has yet to be reported.

SUMMARY OF THE INVENTION

The bistriazene compounds of the present invention are novel alkylating agents which are structurally similar to polyamines such as spermine and spermidine, which interact with DNA. Most currently employed chemotherapeutic alkylating agents interact covalently or noncovalently with the target DNA, after which a crosslinking reaction may occur. The bistriazene compounds of the present invention differ from any known chemotherapeutic agents in that their chemical structure allows them to interact with the DNA molecule while maintaining their chemical integrity. This interaction depends on the formation of multiple hydrogen bonds with the DNA, and in this manner they appear to mimic natural polyamines which normally interact with DNA. In fact, it is possible that due to the structural similarity of the bistriazenes to some of the polyamines, the bistriazenes may occupy the same sites in DNA as the polyamines themselves. Subsequent to this binding, the bistriazenes decompose on the surface of the DNA, releasing the "Linker" in the form of a bisdiazonium ion. This highly reactive substance covalently interacts with the DNA, causing multiple double strand breaks and interstrand crosslinks. As the bisdiazonium ion can be made to vary in its properties by structural modification of the Linker in the bistriazene molecule, the reactivity of the entire molecule can be modulated by appropriate chemical modification. Thus, it appears that bistriazenes may interact with DNA in a polyamine-like fashion, subsequently breaking down to form crosslinking agents which result in the formation of crosslinks lethal to cells. The use of the bistriazene compounds of the present invention as chemotherapeutic drugs therefore confers great specificity of drug interaction with DNA, and because the reactive diazonium ions are formed on the surface of the DNA, delivers a much higher effective dose of the ultimate cytotoxic agent per molecule of administered compound than for simple monodentate drugs. This feature achieves the advantage that the dosage of such bistriazene-based drugs administered will be low in comparison to that of other conventional chemotherapeutic alkylating agents. The combination of specificity and low effective dose portends bistriazene-based anti-cancer drugs with much lower systemic toxicities than those currently in use.

Thus, the bistriazene compounds of the present invention represent an entirely novel class of bidentate, chemotherapeutic alkylating agents with greater specificity and lower toxicity as compared to present treatments.

Accordingly, it is an object of the present invention to provide a bistriazene compound, or a physiologicaly acceptable salt thereof, of the formula:

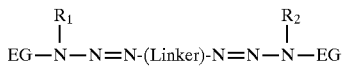

wherein
the Linker is selected from the group consisting of

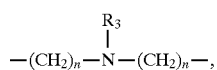

where n=1–5, and $R_3$ is selected from the group consisting of hydrogen and a $C_1$–$C_5$ n-alkyl,

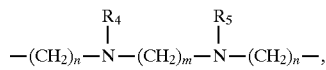

where n=1–5, m=1–5, and $R_4$ and $R_5$ each=$C_1$–$C_5$ n-alkyl,

—$(CH_2)_n$—O—$(CH_2)_n$—, where n=1–5,
—$(CH_2)_n$—S—$(CH_2)_n$—, where n=1–5,
—$(CH_2)_n$—Se—$(CH_2)_n$—, where n=1–5,

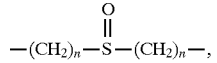

where n=1–5, and
—$(CH_2)_n$—$SO_2$—$(CH_2)_n$—, where n=1–5;
EG is identical or independently selected from the group consisting of a phenyl group, a substituted phenyl group, an arylalkyl group, a substituted arylalkyl group, a condensed ring arylalkyl group, a heterocyclic group, an amine group, and a polyamine.

The final substituent on the triazene moiety, i.e., R or R', is perhaps the most fungible, and may be added following assembly of the basic triazene moiety by methods described for simple dialkyltriazenes (R. H. Smith, Jr., et al., *J. Org. Chem.*, 1986, 51, 3751; R. H. Smith, Jr., et al., *J. Org. Chem.*, 1988, 53, 1467; D. H. Sieh, et al., *J. Am. Chem. Soc.*, 1980, 102, 3883; R. H. Smith, Jr. and C. J. Michejda, *Synthesis*, 1983, 476). R or R' may be identical to EG or to one another, or may be independently selected from the groups comprising hydrogen, alkyl groups, substituted alkyl (including, but not limited to, alkylamines, alkyl ethers and thioethers, haloalkyl, silanes, phosphines, alcohols, amines, etc.) of chain length 1–20, preferably 1–6. R or R' may also include aralkyl or substituted aralkyl (with modifications analogous to those for substituted alkyls), polycyclic aralkyl, aryl groups, and heterocyclic groups of 2–40 non-hydrogen atoms, containing 1–6 rings. Additionally, R may be an acid derivative where the original acid includes, but is not limited to, carboxylic, sulfuric, sulfonic, phosphoric, phosphinic, arsenic, and selenic acids.

R may also include, in the examples cited above, compounds where R equals R', or R is linked to R' such that a cyclic bistriazene compound is formed. Cases where R equals R' may be expanded to include multivalent metals including, but not limited to, palladium, platinum, titanium, zirconium, silicon, selenium, magnesium, and copper. Several metal species such as cisplatin and titanocene dichloride are clinically active as antineoplastic agents, and the bistriazene moiety may serve as a bidentate ligand for these classes of compounds in order to generate compounds with multiple modes of cytotoxic action. If R is linked to R', polymeric compounds may result in addition to cyclic bistriazenes. The polymers produced would have unusual physical properties due to the hydrolytic instability of triazenes. It can be envisioned that this can be used to prepare polymers which could be implanted, and which would hydrolytically decompose to produce active cytotoxic agent in a time release manner. Similarly, it may be that the polymer would only provide a slowly dissolving matrix. This matrix may be used for structural applications, or to release an entrapped substance.

Furthermore, it should be noted that, while for simplicity, all modifications mentioned above have been discussed as being symmetrical, this need not be the case, and asymmetrical bistriazene molecules are encompassed among the compounds of the present invention.

Another object of the present invention is to provide a pharmaceutical composition, comprising an anti-cancer effective amount of said bistriazene compound or physiologically acceptable salt thereof, and a pharmaceutically acceptable carrier.

Yet another object of the present invention is to provide a method for treating cancer in a mammal, including humans, which comprises administering to the subject an anti-cancer effective amount of said bistriazene compound or a physiologically acceptable salt thereof.

A further object of the present invention is to provide a method of inhibiting breakage or digestion of DNA or proteins, comprising treating said DNA or proteins with said bistriazene compound or physiologically acceptable salt thereof.

A still further object of the present invention is to provide a method of producing chemical polymers, comprising treating their monomeric constituents with said bistriazene compound or physiologically acceptable salt thereof.

These objects and others are accomplished in accordance with the present invention by administering an anti-cancer effective amount of a pharmaceutical composition containing a bistriazene compound or a physiologically acceptable salt thereof. Representative bistriazene compounds useful in treating cancer include bis(methyltriazeno)-p-xylene, bis(methyltriazeno)-2-butene, bis(methyltriazeno)ethane, and other bistriazene derivatives which are anti-cancer agents, such as the following:

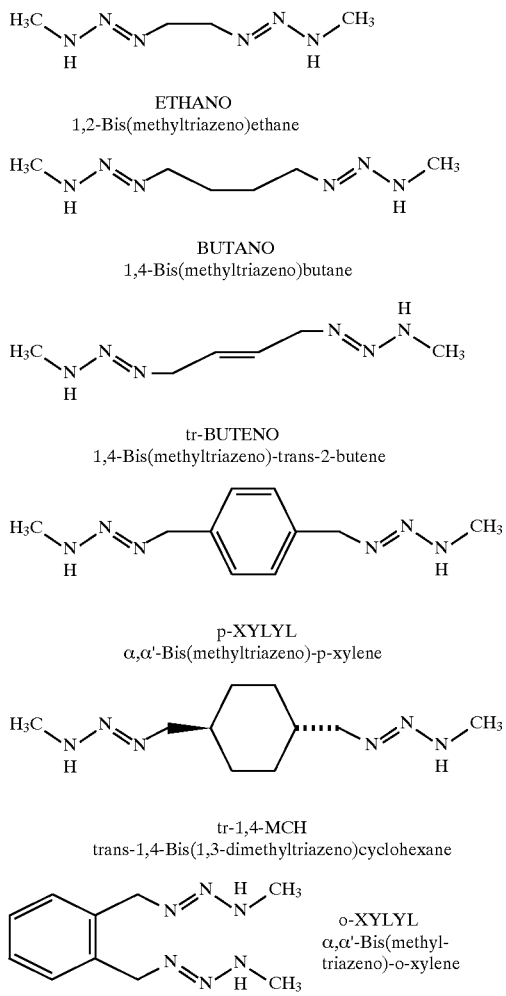

The compounds of the present invention can be used for the treatment of human and animal cancers.

In addition to the use of bistriazene compounds for the therapeutic treatment of neoplastic disease, the use of these compounds as laboratory reagents is also envisioned as another object of the present invention. In the laboratory manipulation of macromolecules such as DNA and proteins, reagents are often employed which interact with the molecule of interest such that the molecule is:

1) Cut in a specific region;
2) Blocked from being enzymatically cut in a specific region;
3) Bound to another molecule with which it is loosely associated;
4) Bound to a matrix such as nitrocellulose or nylon to facilitate handling and probing;
5) Bound to a matrix such as a chromatography support as a ligand for affinity chromatography; or
6) Conjugated to unrelated macromolecules (e.g., toxins to antibodies, antibodies to enzymes, small molecules to oligonucleotide DNA probes, etc.).

Bistriazenes can be adapted for use in these and other laboratory manipulations of macromolecules.

If the bistriazene is modified such that the substituent groups afford a high degree of sequence recognition, then upon alkylation at a labile site, breakage of the DNA or protein backbone may occur (#1 above). Alternatively, alkylation at a stable site may block enzymatic digestion such as restriction enzyme digestion of DNA or protease digestion of proteins (#2 above).

Multifunctional chemical crosslinking agents are presently widely used in applications #3, #5, and #6 cited above. The use of bistriazene compounds in such applications is another object of the present invention.

It is further envisioned that bistriazene compounds will be employed as highly active chemical crosslinking agents useful in immobilizing molecules such as RNA, DNA or proteins on nitrocellulose, nylon, or other similar membranes (application #4, above), thereby facilitating the handling and probing of these biopolymers on such membrane supports.

Yet another object of the present invention is to employ bistriazenes as crosslinking agents in the formation of chemical polymers from their monomeric constituents.

The bistriazene compounds of the present invention may be employed as chemical crosslinking agents in a manner similar to that of other well known crosslinking agents, as would be apparent to one of ordinary skill in the art.

Further scope of the applicability of the present invention will become apparent from detailed description and drawings provided below. However, it should be understood that the detailed description and specific examples, while indicating preferred embodiments of the invention are given by way of illustration only since various changes and modifications within the spirit and scope of the invention will become apparent to those skilled in the art from this detailed description.

BRIEF DESCRIPTION OF THE DRAWINGS

In FIGS. 1–4, the abbreviations of the cell lines represent the following:

CXF, Colon Cancer Xenograft; GXF, Gastric; LXF, Lung: A adeno, L large cell, E epidermoid cell, S small cell; MAXF, Mammary Cancer Xenograft; MEXF Melanoma; PXF, Pleuramesothelioma; SXF, Sarcoma; TXF, Testicular; XF, miscellaneous Cancer Xenograft.

Figure 5:
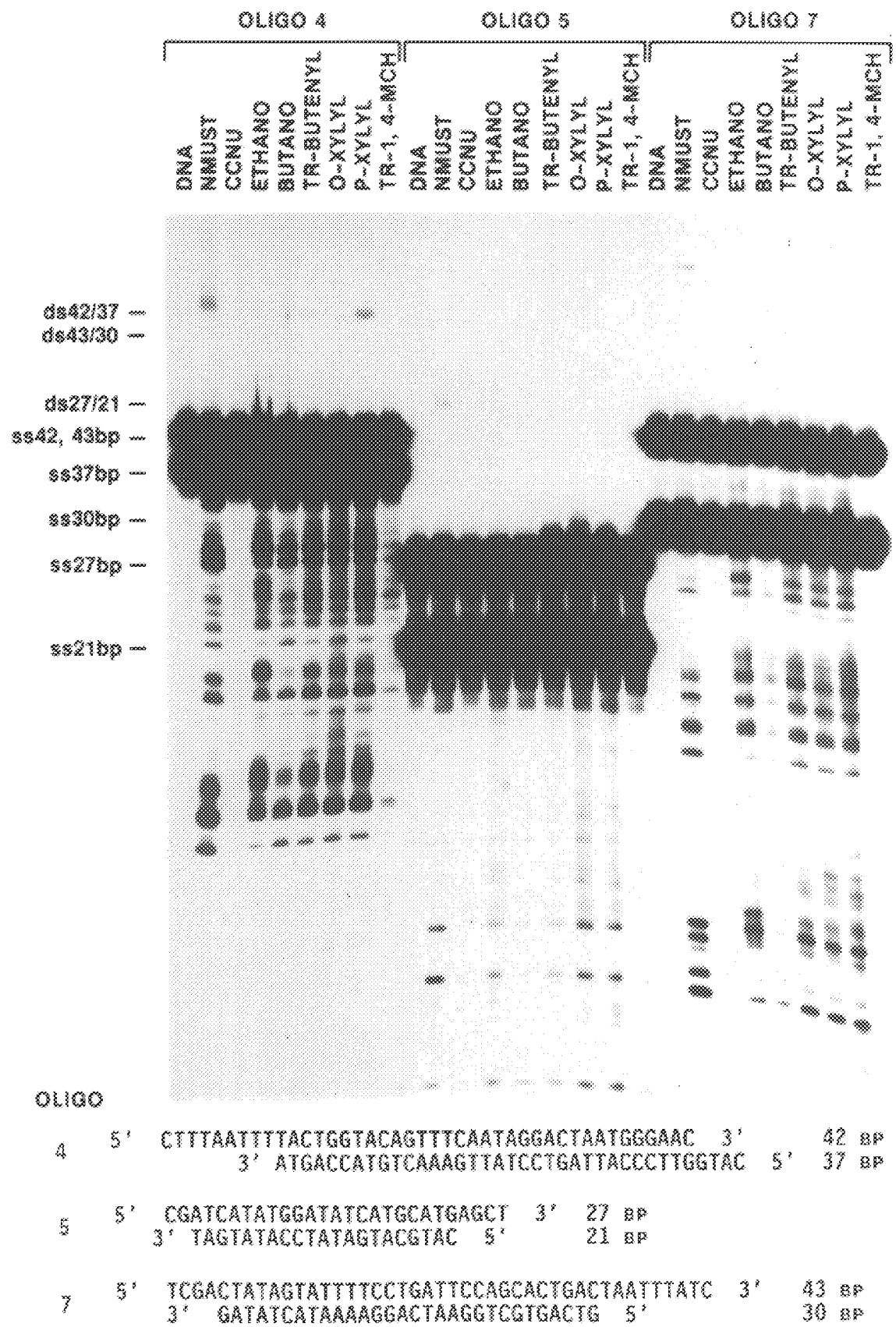

FIG. 5 shows the results of the oligonucleotide crosslinking assay.

Figure 6:
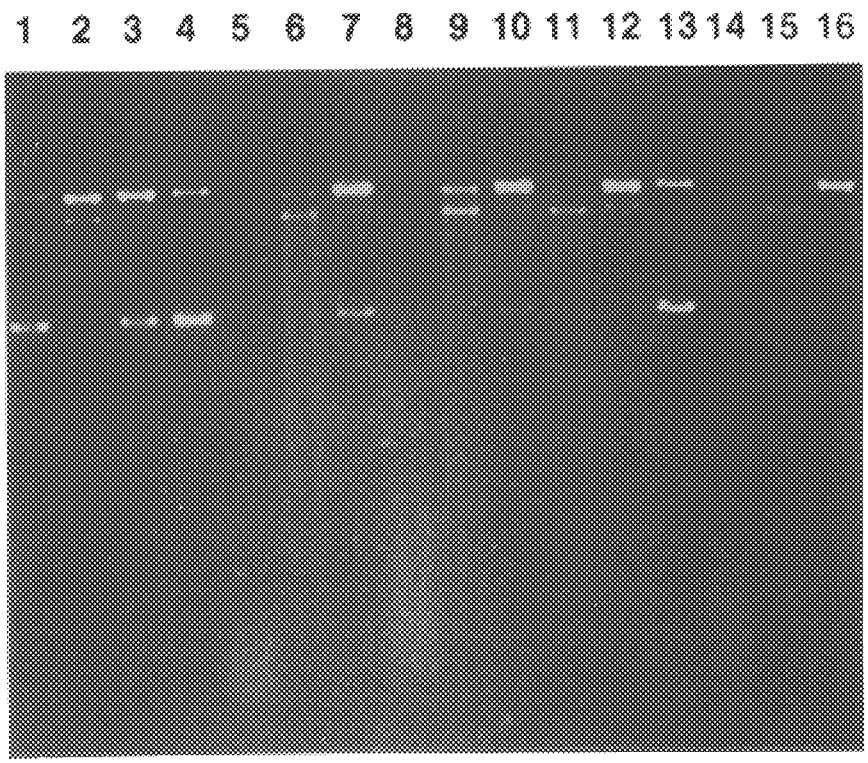

FIG. 6 shows the results of the supercoiled plasmid DNA assay.

Figure 7:
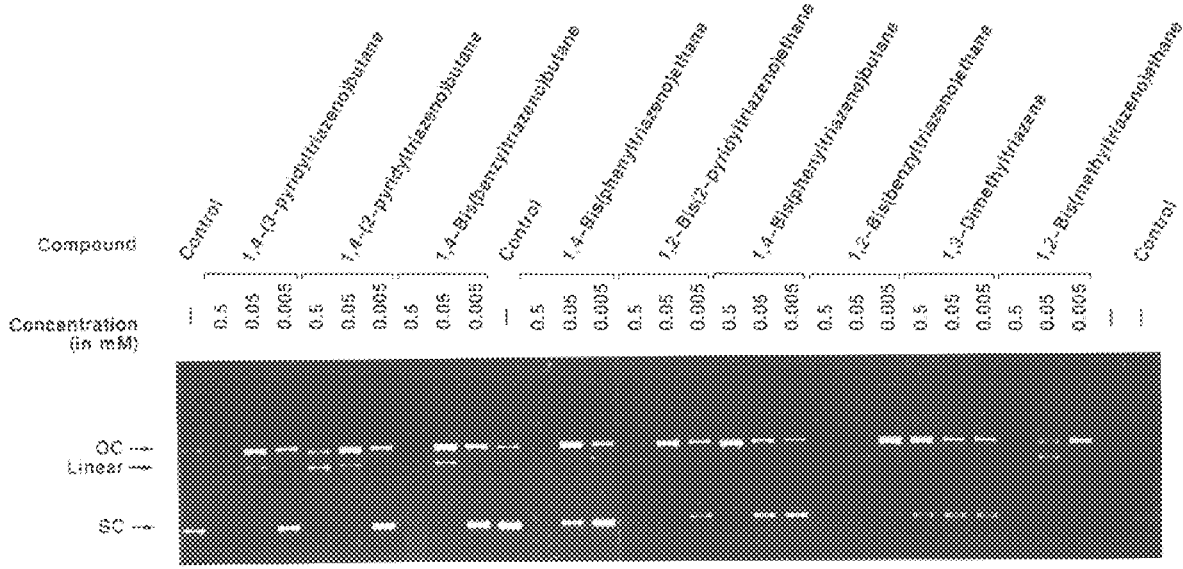

FIG. 7 shows supercoiled plasmid pBR322 treated with various bistriazenes and triazenes indicated in the figure at the concentrations shown. The treated DNA was applied to agarose gels and electrophoresed. Bands were visualized by ethidium bromide staining. The bands of interest are SC=supercoiled plasmid, OC=open circular plasmid, linear= linearized plasmid. An absence of bands in a lane to which DNA had been applied indicates complete destruction of the DNA by the agent at that concentration. Formation of OC requires a single strand break; linearization requires a double strand break.

Figure 8:
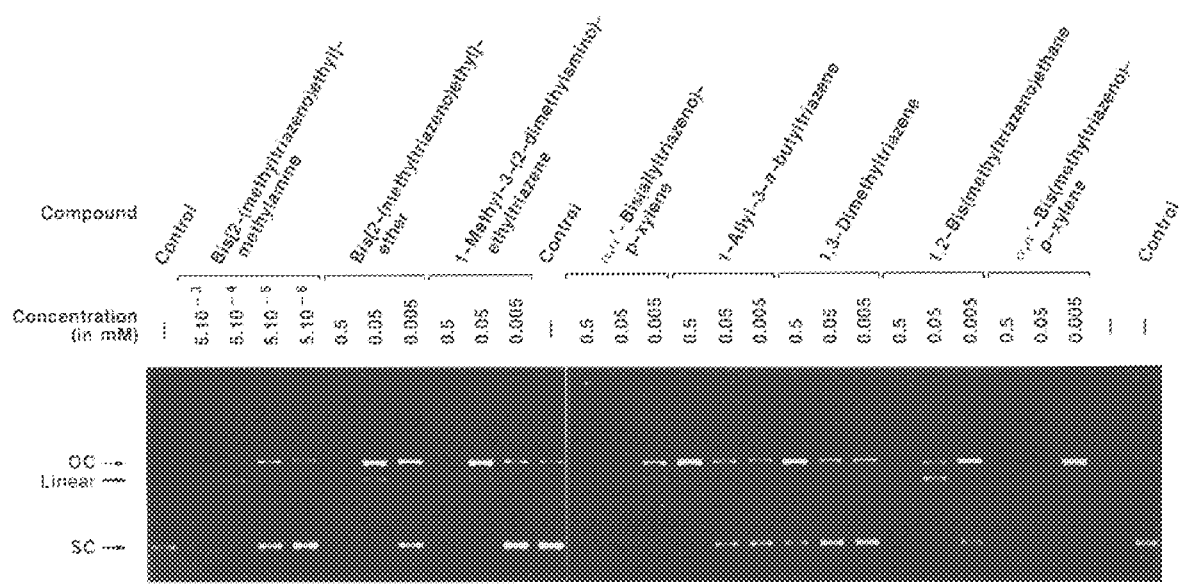

FIG. 8 shows data for the bistriazenes and triazenes indicated, obtained in a manner similar to that in FIG. 7. The applied concentrations of bis[2-(methyltriazeno)-ethyl] methylamine (3) were orders of magnitude lower than those for the other bistriazenes.

DETAILED DESCRIPTION OF THE INVENTION

As those of ordinary skill in the art will recognize, the basic bistriazene structure contains a number of elements which can be modified to affect the desired use of these compounds. These elements are indicated in the following structure:

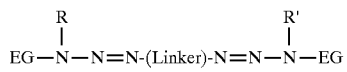

The "Linker" moiety is involved in the structural definition of the molecule and in crosslink formation. The Linker can be either an alkyl group, substituted alkyl (including, but not limited to, alkylamines, alkyl ethers and thioethers, haloalkyl, silanes, phosphines, alcohols, amines, etc.), of chain length 1–20, preferably 2–8. The Linker may also include aralkyl or substituted aralkyl (with modifications analogous to those for substituted alkyls), polycyclic aralkyl, heterocyclic aralkyl, and their substituted derivatives wherein the triazine moieties can be separated by 1–30 carbon atoms, preferably 4–12 carbon atoms. With regard to the "End Group" (EG), this moiety is crucial in modulating the reactivity of bistriazenes. The EGs may be identical or independently selected from groups comprising alkyl groups, substituted alkyl (including, but not limited to, alkylamines, alkyl ethers and thioethers, haloalkyl, silanes, phosphines, alcohols, amines, etc.), of chain length 1–20, preferably 1–6. The EG may also include aralkyl or substituted aralkyl (with modifications analogous to those for substituted alkyls), polycyclic aralkyl, aryl groups and heterocyclic groups of 2–40 non-hydrogen atoms, containing 1–6 rings, including nucleic acid bases and a DNA oligomer(s) bonded to the EG of the bistriazene compound through either the 3' or 5' deoxyribose oxygen of the terminal nucleic acid base.

The final substituent on the triazene moiety, i.e., R or R', is perhaps the most fungible, and may be added following assembly of the basic triazene moiety by methods described for simple dialkyltriazenes (R. H. Smith, Jr., et al., *J. Org. Chem.*, 1986, 51, 3751; R. H. Smith, Jr., et al., *J. Org. Chem.*, 1988, 53, 1467; D. H. Sieh, et al., *J. Am. Chem. Soc.*, 1980, 102, 3883; R. H. Smith, Jr. and C. J. Michejda, *Synthesis*, 1983, 476). R or R' may be identical to EG or to one another, or may be independently selected from the groups comprising hydrogen, alkyl groups, substituted alkyl (including, but not limited to, alkylamines, alkyl ethers and thioethers, haloalkyl, silanes, phosphines, alcohols, amines, etc.) of chain length 1–20, preferably 1–6. R or R' may also include aralkyl or substituted aralkyl (with modifications analogous to those for substituted alkyls), polycyclic aralkyl, aryl groups, and heterocyclic groups of 2–40 non-hydrogen atoms, containing 1–6 rings. Additionally, R may be an acid derivative where the original acid includes, but is not limited to, carboxylic, sulfuric, sulfonic, phosphoric, phosphinic, and arsenic acids.

R may also include, in the examples cited above, compounds where R equals R', or R is linked to R' such that a cyclic bistriazene compound is formed. Cases where R equals R' may be expanded to include multivalent metals including, but not limited to, palladium, platinum, titanium, zirconium, silicon, magnesium, and copper. Several metal species such as cisplatin and titanocene dichloride are clinically active as antineoplastic agents, and the bistriazene moiety may serve as a bidentate ligand for these classes of compounds in order to generate compounds with multiple modes of cytotoxic action. If R is linked to R', polymeric compounds may result in addition to cyclic bistriazenes. The polymers produced would have unusual physical properties due to the hydrolytic instability of triazenes. It can be envisioned that this can be used to prepare polymers which could be implanted, and which would hydrolytically decompose to produce active cytotoxic agent in a time release manner. Similarly, it may be that the polymer would only provide a slowly dissolving matrix. This matrix may be used for structural applications, or to release an entrapped substance.

Furthermore, it should be noted that, while for simplicity, all modifications mentioned above have been discussed as being symmetrical, this need not be the case, and asymmetrical bistriazene molecules are encompassed among the compounds of the present invention.

SYNTHESIS OF BISTRIAZENES

The synthesis of bistriazenes is readily accomplished by the reactions shown below:

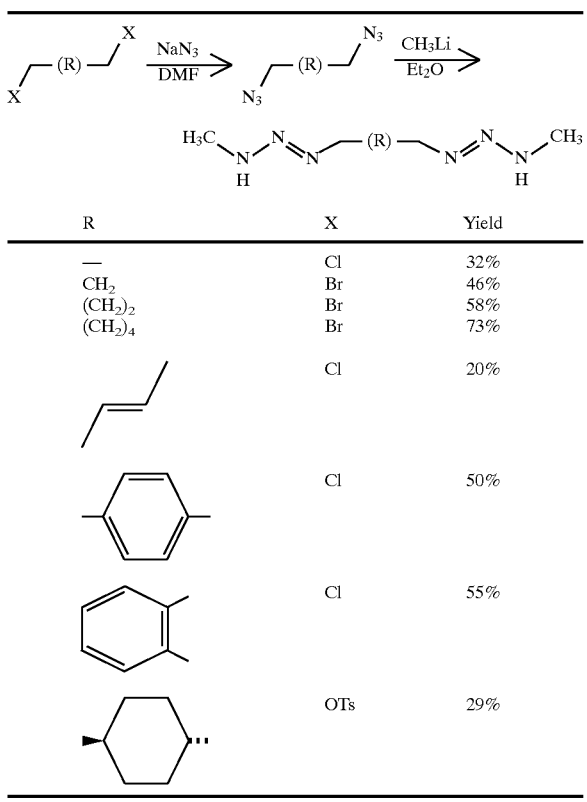

| R | X | Yield |
|---|---|---|
| — | Cl | 32% |
| CH₂ | Br | 46% |
| (CH₂)₂ | Br | 58% |
| (CH₂)₄ | Br | 73% |
|  | Cl | 20% |
|  | Cl | 50% |
|  | Cl | 55% |
|  | OTs | 29% |

In general, bistriazenes are prepared by the reaction of 1,ω-diazidoalkanes with two equivalents of an alkyllithium. The diazidoalkanes are prepared from the corresponding dihaloalkanes and sodium azide in dimethylformamide solution. For example, the simplest bistriazene, 1,2-bis (methyltriazeno)ethane (BMTE), is prepared by the reaction of 1,2-diazidoethane with two equivalents of methyllithium.

In contrast to simple triazenes, bistriazenes are crystalline solids. X-ray crystal structure determination of BMTE reveals that the molecule adopts a conformation in the solid state which maximizes hydrogen bond interactions with its neighbors. In this regard, BMTE is remarkably similar to polyamines such as spermine, spermidine, and their phosphatidyl derivatives, which are known to bind strongly to DNA.

The synthesis and X-ray crystal structure of bistriazenes are described in Blumenstein et al., *Tetrahedron Letters*, submitted for publication, and Blumenstein et al., *Chemical Communications*, submitted for publication, respectively. The synthesis of particular bistriazenes is as follows:

EXAMPLE 1

Trans-1,4-bis(methyltriazenomethyl)cyclohexane

A flask is charged with 3.0 g (6.6 mmole) of trans-1,4-di(methyl 4-toluenesulfonate)cyclohexane, 1.08 g (16.6 mmole) of sodium azide, and 50 ml of dimethylformamide (DMF). The mixture is heated at 50° C. with stirring under argon for 2 days. The mixture is then diluted with 150 ml of water and extracted four times with 40 ml of petroleum ether. The combined organic layers are dried over Na₂SO₄, filtered, and evaporated to afford a pale yellow oil. The residual oil is dissolved in 100 ml of anhydrous ether and cooled to -20° C. under argon. A 1.5M solution of MeLi in ethyl ether (11 ml, 16.5 mmole) is added to the solution over 0.5 hr. A white precipitate begins to form after a small amount of the MeLi has been added. The cooling bath is removed and the mixture is allowed to stir overnight. Excess MeLi is quenched by the careful addition of 30 ml of half-saturated NH₄Cl with cooling of the solution. Vigorous gas evolution accompanies the addition of the first several ml of NH₄Cl, and the addition is carried out as quickly as possible. The aqueous layer is then rapidly separated, washed with 40 ml of water, dried over Na₂SO₄, filtered, and evaporated to afford a pale tan solid. The solid is recrystallized from ether/petroleum ether to yield 430 mg (29% yield) of a white solid, mp 72°–3° C. Mass spectra (FAB) Calc (M+H) 227.1984, Found 227.2017±0.0023.

EXAMPLE 2

1,4-Bis(methyltriazenomethyl)benzene

A flask is charged with 2.0 g (11.4 mmole) of 1,4-di (chloromethyl)benzene, 1.86 g (28.6 mmole) of sodium azide, and 50 ml of DMF. The mixture is heated at 50° C. with stirring under argon overnight. The mixture is worked up and treated with 20 ml of a 1.4M solution of MeLi (28 mmole) as described above. After workup, a yellow solid is obtained. Crystallization from ether/petroleum ether affords 1.26 g (50% yield) of a pale yellow solid, mp 90°–2° C. Mass spectra (FAB) Calc (M+H) 221.1514, Found 221.1558±0.0022.

EXAMPLE 3

1,2-Bis(methyltriazenomethyl)benzene

A flask is charged with 7.96 g (45 mmole) of 1,2-di (chloromethyl)benzene, 7.39 g (114 mmole) of sodium azide, and 150 ml of DMF. The mixture is heated at 50° C. with stirring under argon overnight. The mixture is worked up, and in 300 ml of anhydrous ether, is treated with 90 ml of a 1.3M solution of MeLi (117 mmole) as described above. After workup, a yellow-orange oil is obtained. Kugelrohr distillation (110°–120° C., 0.5 mm) affords 5.40 g (55% yield) of a pale yellow oil which darkened and became a semi-solid upon standing. Mass spectra (FAB) Calc (M+H) 221.1514, Found 221.1513±0.0022.

EXAMPLE 4

1,4-Bis(methyltrizeno)butane

A flask is charged with 4.0 g (18.5 mmole) of 1,4-dibromobutane, 3.6 g (55 mmole) of sodium azide, and 50 ml of DMF. The mixture is heated at 50° C. with stirring under argon overnight. The mixture is worked up and treated with 45 ml of a 1.3M solution of MeLi (58 mmole) as described above. After 3 hr the reaction is worked up as described above, and a yellow solid is obtained. Crystallization from ether/petroleum ether affords 1.86 g (58% yield) of a white solid, mp 40°–2° C. Mass spectra (FAB) Calc (M+H) 173.1514, Found 173.1510±0.0017.

EXAMPLE 5

1,2-Bis(methyltriazeno)ethane

A flask is charged with 5.0 g (27 mmole) of 1,2-dibromoethane, 3.8 g (58 mmole) of sodium azide, and 50 ml of DMF. The mixture is heated at 50° C. with stirring under argon overnight. The mixture is worked up as described above, except that the azide solution is not evaporated down totally. When about 30 ml of solution remains the mixture is treated with 45 ml of a 1.3M solution of MeLi (58 mmole) as above. After 3 hr the reaction is worked up as described above, and a yellow solid is obtained. Crystallization from ether/petroleum ether affords 1.23 g (32% yield) of an off-white solid, mp 64°–6° C. Mass spectra (FAB) Calc (M+H) 145.1201, Found 145.1220±0.0015.

EXAMPLE 6

1,6-Bis(methyltriazeno)hexane

A flask is charged with 10.0 g (41 mmole) of 1,6-dibromohexane, 6.66 g (102 mmole) of sodium azide, and 100 ml of DMF. The mixture is heated at 50° C. with stirring under argon overnight. The mixture is worked up and as a solution in 400 ml of anhydrous ether, is treated with 77 ml of a 1.3M solution of MeLi (100 mmole) as described above. After 3 hr the reaction is worked up as described above, and a yellow solid is obtained. Crystallization from ether/petroleum ether affords 5.96 g (73% yield) of a white solid, mp 54°–5° C.

EXAMPLE 7

1,4-Bis(methyltriazeno)-trans-2-butene

A flask is charged with 12.5 g (100 mmole) of 1,4-dichloro-trans-2-butene, 14.3 g (220 mmole) of sodium azide, and 200 ml of DMF. The mixture is stirred under argon overnight, worked up, and as a solution in 400 ml of anhydrous ether, is treated with 130 ml of a 1.4M solution of MeLi (183 mmole) as described above. After 3 hr the reaction is worked up, and a yellow solid is obtained. Crystallization from ether/petroleum ether affords 3.34 g (20% yield) of a pale yellow solid, mp 71°–4° C. Mass spectra (FAB) Calc (M+H) 171.1358, Found 171.1397±0.0017.

EXAMPLE 8

1,6-Bis(methyltriazeno)propane

A flask is charged with 10.0 g (49.5 mmole) of 1,3-dibromopropane, 7.08 g (109 mmole) of sodium azide, and 100 ml of DMF. The mixture is stirred under argon overnight, worked up, and as a solution in 400 ml of anhydrous ether, is treated with 80 ml of a 1.4M solution of MeLi (112 mmole) as described above. After 3 hr the reaction is worked up as described above, and a yellow solid is obtained. Crystallization from ether/petroleum ether affords 3.61 g (46% yield) of a white solid, mp 55°–7° C. Mass spectra (FAB) Calc (M+H) 159.1358, Found 159.1360±0.0016.

EXAMPLE 9

1,2-diazidoethane and 1,4-diazidobutane

The procedures described in Examples 4 and 5, above, were followed.

EXAMPLE 10

1,2-Bis(phenyltriazeno)ethane

A solution of 1.12 g (10 mmoles) of 1,2-diazidoethane in 10 ml. of tetrahydrofuran (THF) was cooled to −45° C. To this was added dropwise with stirring 15 ml. of 2.0M phenylmagnesium chloride in THF, and stirring was continued overnight with the temperature being allowed to rise slowly to ambient. The reaction mixture was diluted with 200 ml. of diethylether and the ether solution was washed first with 30 ml. of 10% ammonium chloride in 10% ammonium hydroxide, followed by water (3×30 ml.), and then dried over anhydrous sodium sulfate. The solvent was distilled off leaving 2.50 g of a pale yellow residue. This was redissolved in 40 ml. of ether and allowed to crystallize slowly, which resulted in 1.20 g of powdery crystals, m.p. 125°–127° C. (dec.). The material migrated as a single spot on TLC and the nmr and the mass spectra were fully consistent with the structure.

EXAMPLE 11

1,4-Bis(phenyltriazeno)butane

A reaction of 1.40 g (10.0 mmoles) of 1,4-diazidobutane with 30 mmoles of phenylmagnesium chloride in 15 ml. of THF was carried out in an identical fashion to the foregoing example of 1,2-bis(phenyltriazeno)ethane. The residue following the evaporation of the ether weighed 2.8 g. This was crystallized from THF/ether mixture and then recrystallized from THF/benzene (2:1) to produce 1.34 g of white crystals, m.p. 116°–118° C. (dec.). This material was poorly soluble in diethylether and only soluble in warm (50° C.) benzene, and freely in THF. The nmr and mass spectra were fully consistent with the structure.

EXAMPLE 12

1,4-Bis(benzyltriazeno)butane

A solution of 1.40 g (10 mmoles) of 1,4-diazidobutane, in 10 ml. of THF and chilled to −45° C., was treated dropwise with 15 ml of 2.0M benzylmagnesium chloride in THF (30 mmoles). The reaction mixture was magnetically stirred overnight at room temperature. The solvent was removed under vacuum and the residue was dissolved in 200 ml. of diethylether and washed with 30 ml. of ammonium buffer (50 g. ammonium chloride, 178 ml. of 10% ammonium hydroxide and 272 ml. of water), followed by 2×30 ml of water. The solution was dried over sodium sulfate and concentrated on a rotary evaporator and dried under high vacuum at room temperature. The crude product was recrystallized from diethylether in the −20° freezer to produce 2.6 g. of white crystals m.p. 71°–74° C. The nmr and mass spectra were fully consistent with the structure.

EXAMPLE 13

1,2-Bis(benzyltriazeno)ethane

A solution of 1.12 g (10 mmoles) of 1,2-diazidoethane in 20 ml. of THF was cooled to −60° C. This solution was treated with 15 ml of 2.0M benzylmagnesium chloride in THF (30 mmoles) dropwise with stirring. The reaction mixture was allowed to come to room temperature slowly, and was then cooled again to −60° C., and 10 ml. of ammonium buffer (see preparation above) was added and the reaction was allowed to come to room temperature. The reaction mixture was mixed with 100 ml. of diethylether and the organic layer was separated, dried over anhydrous sodium sulfate, and the solvent was removed on a rotary evaporator. The pink residual oil was subjected to high vacuum overnight, which produced a pale yellow solid. This material was crystallized from ether/pentane (1:1) to produce 1.71 g of colorless powdery solid m.p. 73°–75° C. Spectroscopy (nmr and mass) were consistent with the structure.

EXAMPLE 14

1,4-Bis(2-pyridyltriazeno)butane

A solution of 3.95 g (25 mmoles) of 2-bromopyridine in 20 ml of dry pentane was added dropwise to 10 ml. of 2.5M butyllithium in hexane at −78° C. To the resulting yellow slurry was added dropwise with stirring 1.75 g (12.5 mmoles) of 1,4-diazidobutane in 10 ml. of pentane. Stirring was continued for 2 hr. at −78° and then the reaction mixture was allowed to warm to room temperature. The reaction mixture was treated with 60 ml. of ammonium buffer which caused a precipitate to appear after the reaction was cooled to −78° C. The solid was filtered off. It was poorly soluble in common solvents such as halomethanes, acetone, methanol and water. It was sparingly soluble in dimethylsulfoxide. The yield was 2.3 g., m.p. 133–136. Spectroscopic data were consistent with the structure.

EXAMPLE 15

1,2-Bis(2-pyridyltriazeno)ethane

A solution of butyllithium in hexane (5 ml., 2.5M) was dissolved in 10 ml. of tetrahydrofuran and cooled to −78° C. To this was added dropwise with stirring a solution of 1.98 g (12.5 mmoles) of 2-bromopyridine in 10 ml. of tetrahydrofuran. The dark yellow solution of the pyridine anion was mixed with a solution of 0.70 g (6.2 mmoles) of 1,2-diazidoethane in 10 ml. of tetrahydrofuran at −78° C. After 1 hr. of stirring the dark green solution was treated with 10 ml. of ammonium buffer. The color changed to yellow. The organic solvent was removed in vacuo, and the precipitate was isolated by filtration and washed with copious quantities of diethylether. The powdery material was finally dried under high vacuum. The yield was 770 mg. This material was not soluble in most solvents, except dimethylsulfoxide. It did not have a sharp melting point since decomposition began before it was reached (rapid above 100° C.). The spectra, however, were fully consistent with the structure.

EXAMPLE 16

1,4-Bis(3-pyridyltriazeno)butane

To 12.5 mmoles of butyllithium in hexane (5 ml. of 2.5M butyllithium diluted with 10 ml. of hexane) and chilled to −90° C. (acetone & liquid nitrogen) was added dropwise 1.978 (12.5 mmoles) of 3-bromopyridine in 10 ml. of hexane. The reaction was further diluted with 20 ml. of hexane to aid stirring at −75° C. for 2 hr. and was then treated with 0.876 g. (6.25 mmoles) of 1,4-diazidobutane. The reaction mixture was allowed to stir at room temperature overnight. It was then chilled to −40° C. and treated with 10 ml. of the ammonium buffer. This produced two layers and a polymer-like precipitate. The mixture was diluted with 100 ml. of hexane and the layers were separated. The organic phase was washed with water (2×20 ml.) and was dried over sodium sulfate. After removal of solvent in vacuo, 0.98 g of oily residue was obtained. This did not contain the desired product. The polymer-like solid, however, was triturated with 30 ml. of diethylether overnight. This resulted in the formation of a pale yellow microcrystalline material, which was filtered and dried under high vacuum. The yield was 0.40 g. of pure bistriazene, which decomposed before melting. The nmr and mass spectra, however, were fully consistent with the structure.

EXAMPLE 17

1,2-Bis(3-pyridyltriazeno)ethane

A solution of 5 ml. of 2.5M butyllithium in hexane, diluted further with 10 ml. of hexane, was chilled to −90° C. This was treated by dropwise addition with 1.97 g (12.5 mmoles) of 3-bromopyridine in 10 ml. of hexane. The yellow slurry was stirred at −60° C. for 1 hr. and then treated by dropwise addition with 0.70 g (6.2 mmoles) of 1,2-diazidoethane. The solution remained yellow, and was stirred at room temperature overnight. The reaction mixture was then treated with ammonium buffer and the solvents were removed in vacuo. The residue was treated with 50 ml. of diethylether and 10 ml. of water overnight. The residual powder was virtually pure product in a yield of 120 mg (pale orange). The product migrated as a single spot on thin layer chromatography and the nmr and mass spectra were fully consistent with the structure.

EXAMPLE 18

Bis[2-(methyltriazeno)ethyl]ether

A flask was charged with 2.08 g (14 mmole) of bis(2-chloroethyl)ether, 2.73 g (42 mmole) of sodium azide, and 150 ml of dimethylformamide. The mixture was heated at 50° C. with stirring under argon for 5 days. The mixture was then diluted with 250 ml of water and extracted four times with 50 ml of pentane. The combined organic layers were dried over sodium sulfate, filtered, and concentrated to afford approximately 25 ml of a solution of the diazide in pentane. The solution was diluted with 100 ml of anhydrous ether and cooled to −20° C. under argon. A 3.0M solution of methyl magnesium bromide in ethyl ether (14 ml, 42 mmole) was added to the solution over 0.5 hr. A white precipitate began to form after a small amount of the reagent had been added. The cooling bath was removed and the mixture was allowed to stir for 2 hr. Excess Grignard reagent was quenched by the careful addition of 50 ml of half-saturated ammonium chloride with cooling of the solution. Vigorous gas evolution accompanied the first several milliliters of ammonium chloride, but the addition was carried out as fast as possible. The aqueous layer was then rapidly separated and washed with 50 ml of pentane. The organic layers were combined, dried over sodium sulfate, filtered and evaporated to afford a pale tan solid. The solid was recrystallized from ether/petroleum ether to yield 1.28 g of a white solid. $^1$H NMR(CDCl$_3$, 200 MHz): 3.195 (br, 4 H), 3.679 (br, 6 H), 7.32 (br, 2 H).

EXAMPLE 19

Bis[2-(methyltriazeno)ethyl]methyl amine

A flask was charged with 2.0 g (10.4 mmole) of bis(2-chloroethyl)methyl amine hydrochloride, 2.03 g (31.2 mmole) of sodium azide, and 100 ml of dimethylformamide. The mixture was heated at 50° C. with stirring under argon for 5 days. The mixture was then diluted with 150 ml of 2.5% aqueous sodium hydroxide solution and extracted four times with 50 ml of pentane. The combined organic layers were dried over sodium sulfate, filtered, and concentrated to afford approximately 25 ml of a solution of the diazide in pentane. The solution was diluted with 100 ml of anhydrous ether and cooled to −20° C. under argon. A 3.0M solution of methylmagnesium bromide in ethyl ether (10.4 ml, 31.2 mmole) was added to the solution over 0.5 hr. A white precipitate began to form after a small amount of the reagent had been added. The cooling bath was removed and the mixture was allowed to stir for 2 hr. Excess reagent was quenched by the careful addition of 50 ml of 2.5% NaOH with cooling of the solution. Vigorous gas evolution accompanied the first several milliliters of sodium hydroxide but the addition was carried out as fast as possible. The aqueous layer was then rapidly separated and washed with 50 ml of pentane. The organic layers were combined, dried over sodium sulfate, filtered and evaporated to afford a yellow oil. The oil was distilled under vacuum using a kugelrohr apparatus at 0.1 mm Hg with a pot temperature of 80°–120° C. to yield 3.120 g of a clear oil. $^1$H NMR (CDCl$_3$, 200 MHz): 2.67 (br), 2.652 (br), 2.962 (br), 3.406 (br), 3.708 (br), 7.412 (br), 7.716 (br).

BIOLOGICAL ACTIVITY

The bistriazene compounds of the present invention are useful in the treatment of a wide variety of cancers, as shown from the data below.

Clonogenic Assay. The response of a variety of human tumor cell lines to bistriazenes was determined via the clonogenic assay described in Fiebig et al. (1987) *European Journal of Cancer and Clinical Oncology* 23: 937–948.

Briefly, the assay system consists of a modified, two-layer soft agar culture system. The bottom layer consists of 1 ml of modified Dulbecco medium supplemented with L-glutamine, containing 10% fetal calf serum and 0.5% agar, in a 35 mm petri-dish. The upper layer contains 2–5×10$^5$ viable human tumor cells suspended in a 1 ml volume, consisting of 0.3% agar, 30% fetal calf serum, and the medium. The drugs to be tested, contained in 1 ml of medium containing 30% fetal calf serum, are included in the upper layer. Control plates are identical, except for the omission of the drugs. The plates are incubated at 37° C. in a humidified atmosphere containing 7% carbon dioxide for varying periods (7–21 days). The time in culture is determined by the rate of colony formation in the control plates. At the end of the culture period, the number of colonies in the drug treated cultures is compared to the number of colonies in the control plates, after visualization of the live colonies by staining with tetrazolium chloride.

Three different bistriazenes were examined in the assay. In all cases, the End Group (EG) was methyl, while the Linker was varied:

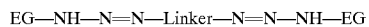

Linker

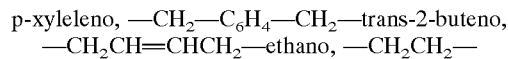

Each of these compounds was evaluated against a panel of human tumor cells, the identity of which is indicated in FIGS. 1–4. The tumors included those derived from colon cancer, three types of lung cancer, mammary cancer, ovarian cancer, two types of kidney cancer, a mesothelioma, a gastric cancer, and a sarcoma. These tumors represent some of the most important cancers for which current treatments are inadequate. For comparison, the assays of the various bistriazenes were compared to the response induced in the same tumors by DTIC, a drug employed in clinical practice.

Figure 1:
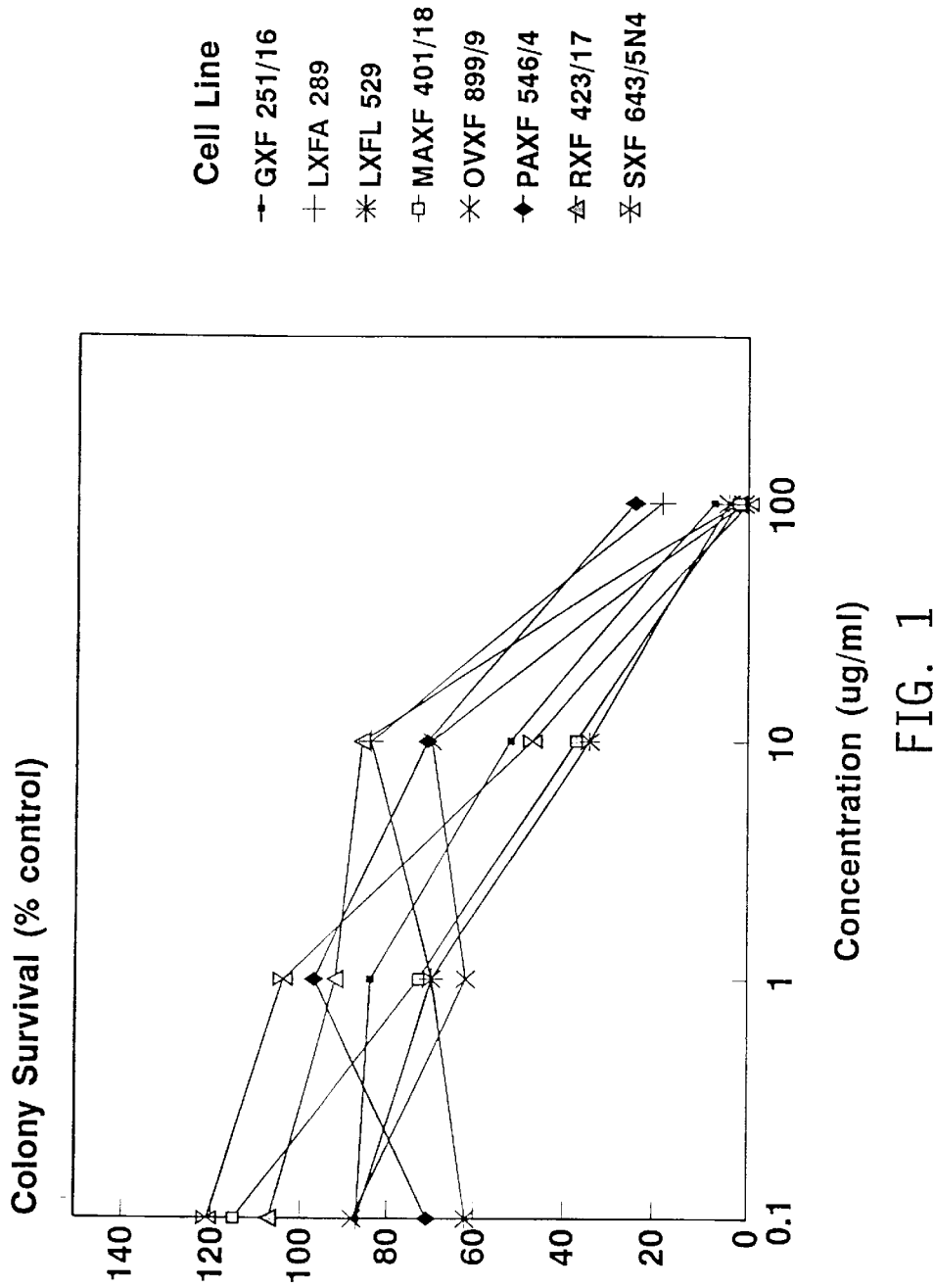
FIG. 1 shows the survival in vitro of several human tumor cell lines exposed to various concentrations of bis (methyltriazeno)-p-xylene.

FIG. 1 shows dose-response curves obtained in the in vitro clonogenic cytotoxicity assay against several human tumor cell lines employing bis(methyltriazeno)-p-xylene. At a dose of 100 ug/ml, this compound was highly toxic to all tumor cell lines. At a dose of 10 ug/ml, it exhibited toxicity against approximately half of the cell lines examined. Some activity was also evident at a dose of 1 ug/ml in about half the cell lines.

Figure 2:
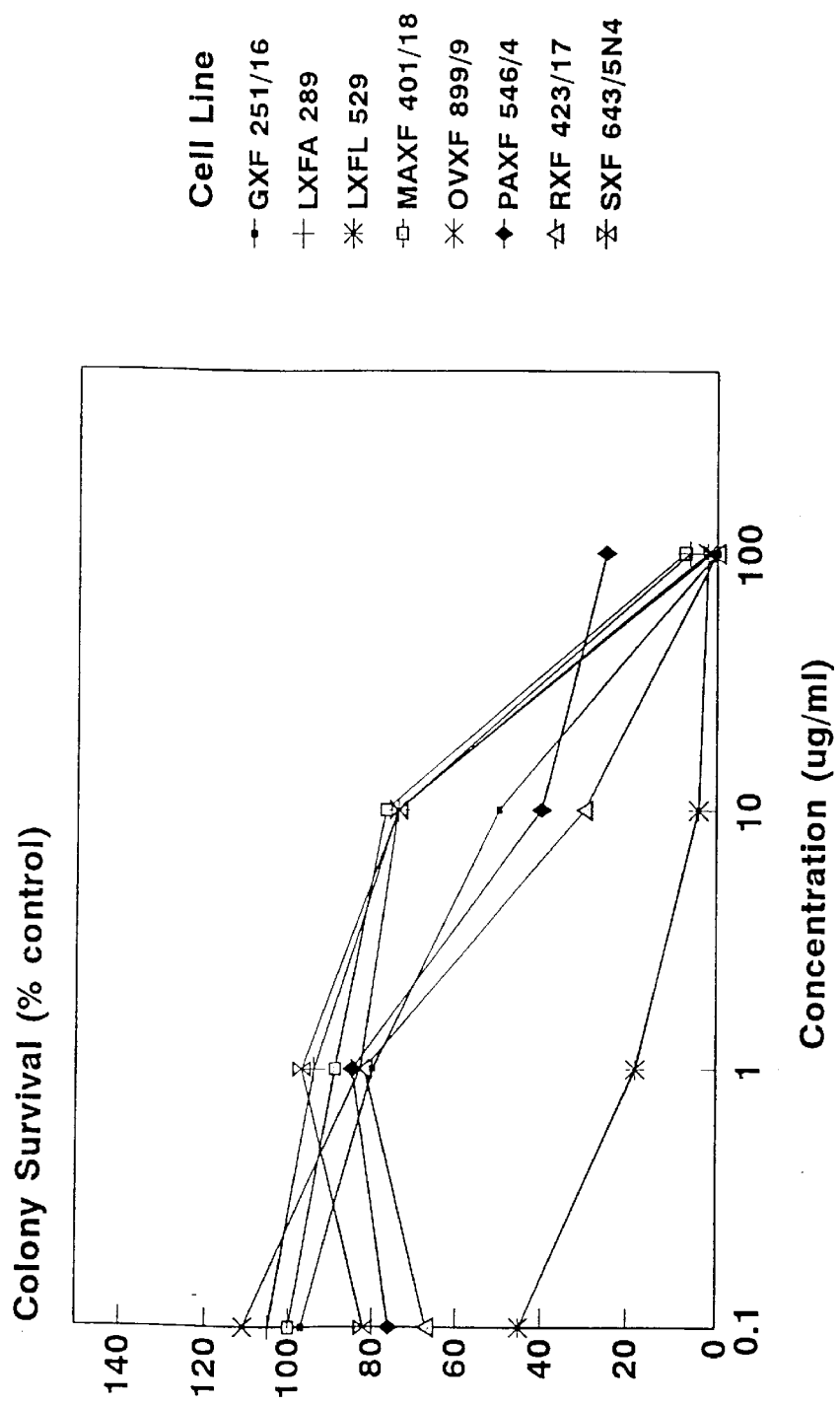
FIG. 2 shows the survival in vitro of several human tumor cell lines exposed to various concentrations of bis (methyltriazeno)-2-butene.

The data in FIG. 2 disclose the results obtained with 1,4-bis(methyltriazeno)-trans-2-butene. This drug exhibited potent cytotoxic activity against all the tumors tested at 100 ug/ml. This activity persisted at 10 ug/ml, especially for the large cell lung carcinoma LXFL529 and the renal cancer RXF423/17. At a dose of 1 ug/ml, there was still significant activity against the lung cancer. Thus, 1,4-bis (methyltriazeno)-trans-2-butene is a potently active compound, the cytotoxic activity of which is highly specific for certain types of cancers.

Figure 3:
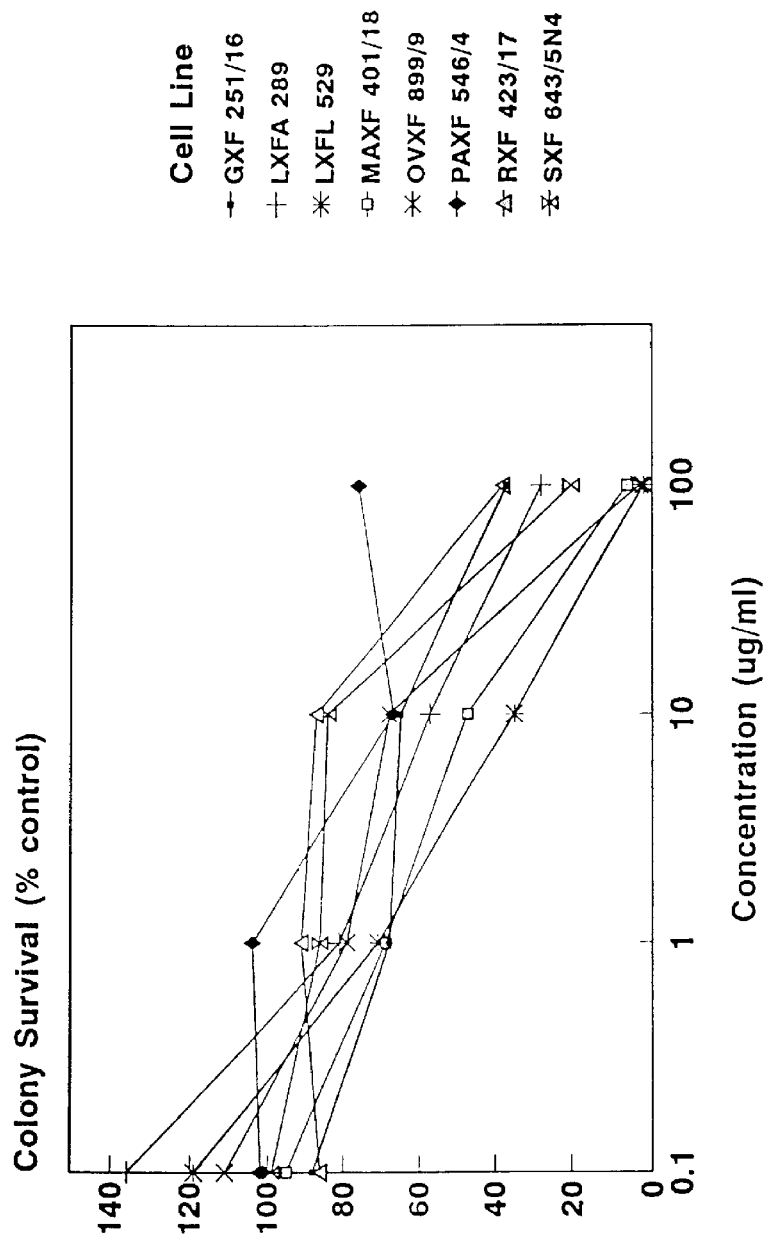
FIG. 3 shows the survival in vitro of several human tumor cell lines exposed to various concentration of bis (methyltriazeno)ethane.

FIG. 3 discloses the results obtained with bis (methyltriazeno)ethane in the clonogenic assay. This compound was highly cytotoxic at 100 ug/ml to most of the tumor cell lines. Relatively little or no activity was observed, however, in the mesothelioma, the gastric carcinoma, or the renal cancer RXF 423/17. At 10 ug/ml, only marginal, but significant, activity was seen in the large cell lung cancer and in the mammary cancer.

Figure 4:
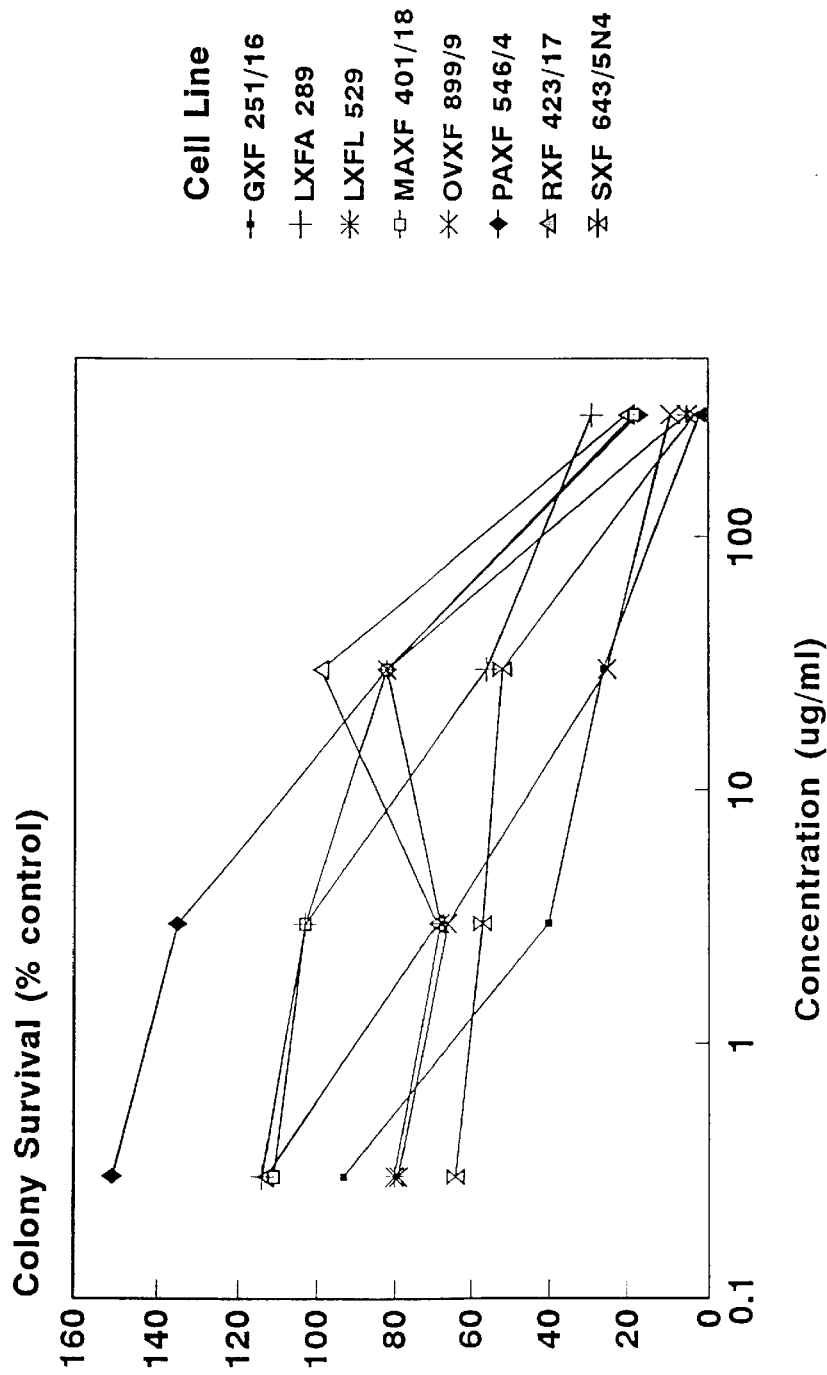
FIG. 4 shows the survival in vitro of several human tumor cell lines exposed to various concentrations of 5-(3,3-dimethyltriazeno)imidazole-4-carboxamide (DTIC).

For comparative purposes, the activity of DTIC (5-(3,3-dimethyltriazeno)imidazole-4-carboxamide) was tested in these cell lines. The results are shown in FIG. 4. DTIC is used clinically against metastatic melanoma, non-Hodgkins lymphoma, and soft-tissue sarcomas. At each point, the dose of DTIC was 3 times larger than that of the bistriazenes. Thus, at 300 ug/ml, DTIC was potently cytotoxic on all cell lines. At 30 ug/ml, it showed activity against the gastric carcinoma GXF251/16 and the ovarian cancer OVXF899/9. At 3 ug/ml, it exhibited marginal activity against the gastric cancer. Thus, all of the bistriazenes tested in this assay were at least as potent as DTIC. The bistriazene 1,4-bis (methyltriazeno)-trans-2-butene is highly potent against several tumors, especially the large cell lung carcinoma.

It may be concluded from these data that bistriazenes, as a class of compounds, are cytotoxic agents which exhibit considerable selectivity toward certain tumors. It is also clear from these data that the nature of the Linker is of paramount importance in modulating the activity and selectivity of cytotoxic action of these compounds. The clonogenic assay system facilitates rapid testing of the anti-tumor activities of newly synthesized bistriazenes containing systematically varied EG's and Linkers, in order to establish the chemical and biological characteristics which will result in additional useful drugs.

CHEMICAL ACTIVITY

Crosslinking of Oligonucleotides: The reaction of bistriazenes can afford interstrand crosslinks if the triazene decomposition produces alkydiazonium ions at each end of the Linker chain.

Bistriazenes react with varying efficiency with different oligonucleotides. Unsaturated bistriazenes such as p-xylyl and trans-butenyl produce stable crosslinked species in oligonucleotides. The amount of crosslinked species varies with the oligonucleotide sequence. The level of crosslinking is comparable to that seen with nitrogen mustard, and exceeds that observed with 1-(2-chloroethyl)-3-cyclohexyl-1-nitrosourea.

The crosslinking of oligonucleotides by bistriazenes was demonstrated in the following assay system:

A solution of 6.2 ng of $^{32}$P-endlabeled oligonucleotide in 0.1M cacodylic acid buffer (0.1M NaCl, pH 7.4) was allowed to react with the desired compound dissolved in 1/10 volume DMSO. Final concentrations of the compounds in the oligonucleotide solution were 0.1 mM NMUST, 1.0 mM CCNU, or 10 mM bistriazene. Reactions were incubated at 37° C. for 42 hours, and analyzed by denaturing polyacrylamide gel electrophoresis (20% gel) followed by autoradiography. the gels were intentionally overexposed to better visualize bands corresponding to interstrand crosslinks. Large amounts of unreacted oligonucleotides were also visualized under these conditions.

As shown in FIG. 5, the results obtained with nitrogen mustard and the p-xylyl bistriazene derivative demonstrate that the oligonucleotides were stably covalently crosslinked by both the nitrogen mustard, a known crosslinking agent, as well as by the p-xylyl bistriazene of the instant invention. As can also be seen from FIG. 5, CCNU, a clinically employed DNA interstrand crosslinking agent, was not as effective at forming crosslinks as the p-xylyl bistriazene derivative.

All compounds examined caused extensive DNA strand breakage, because of which labile adducts were not observable.

Plasmid DNA Strandbreaking. DNA strand breaks may occur via the hydrolysis of labile alkylation sites. A single strand break allows the relaxation of supercoiled DNA to afford a nicked open circular form. Double strand breakage producing linear plasmid DNA occurs upon the hydrolysis of two labile alkylation sites close to one another on opposite DNA strands. These alkylation events may be either an interstrand crosslink, or discrete, but closely located, monoalkylations.

Dialkyltriazenes afford more strand breakage than alkylsulfates and sulfonates. Bistriazenes are approximately 10–200 times more efficacious at producing strand breaks than dialkyltriazenes. Bistriazenes afford significant quantities of linear DNA, whereas simple dialkyltriazenes produce only small amounts of the linear form, and only traces are detectable in the reaction of alkylsulfates with plasmid DNA. Restriction endonuclease treatment of bistriazene-modified DNA suggests that linearization is not highly specific for sequences on the plasmid.

The supercoiled plasmid strand break assay was carried out in a solution of 0.15 ug of pBR322 DNA in 9.5 ul of TE buffer (10 mM) Tris, 0.1, mM EDTA, pH 7.4) prepared at room temperature. A 0.5 ul aliquot of compound in DMSO was added, the solution vortexed lightly, and the samples incubated at 37° for 48 hours. Loading buffer (2 ul, 40% glycerol, and 1% bromphenol blue in TAE buffer) was added to each sample, and a 3 ul aliquot was analyzed by agarose gel electrophoresis (0.9% gel, 1.5 ug ethidium bromide/ml gel), and visualized by fluorescence.

The experimental results shown in FIG. 6 indicate that the bistriazenes examined afford higher levels of DNA modification than do simple dialkyltriazenes such as dimethyltriazene, and that the bistriazenes afford far more linearized DNA, indicated labile alkylation events on opposite strands of the DNA in close proximity to one another. These alkylation events may be a labile interstrand crosslink or discrete alkylation events near one another on opposite strands.

This suggests interaction of the bistriazine with DNA prior to forming active alkylating agent rather than simple hydrolysis to alkyldiazonium ion.

BISTRIAZENES POSSESSING ENHANCED CHEMICAL STABILITY AND THE SAME OR GREATER CYTOTOXIC EFFECTS

The bistriazenes described above are highly chemically reactive. It was therefore deemed desirable to prepare bistriazenes possessing the same or greater cytotoxic effects, but which are more stable chemically. The rationale for the preparation of such bistriazenes is described below.

The bistriazenes described supra have $-CH_3$ (methyl) as the EG. Since the EGs appeared to have little influence on the reactivity of these molecules toward DNA, it was reasoned that they could be employed to modulate the reactivity of bistriazenes. It was further reasoned that electron attracting groups would increase the chemical stability of the bistriazenes. Accordingly, bistriazenes, where the linker was ethano [$(CH_2)_2$] or butano [$(CH_2)_4$], and the EG groups were phenyl ($C_6H_5$) or benzyl ($C_6H_5CH_2$), were prepared. These compounds proved to be much more stable toward decomposition than those where the EG was methyl. It was further reasoned that the stability of bistriazenes could be enhanced even more if the EG could be protonated at physiological pH. The reason for this hypothesis is that if the EG had a positive charge, it would be much more difficult to decompose the bistriazene molecule since this reaction requires the addition of a proton to the triazene moiety. The bistriazenes bis(3-pyridyltriazeno)ethane (1a), bis(3-pyridyltriazeno)butane (1b), and the isomeric bis(2-pyridyltriazeno)ethane (2a) and bis(2-pyridyltriazeno) butane (2b) were prepared by the reaction of the corresponding pyridyl lithium with 1,2-diazidoethane or 1,4-diazidobutane via procedures described above.

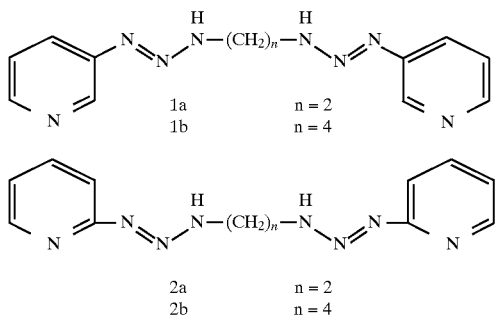

1a  n = 2
1b  n = 4

2a  n = 2
2b  n = 4

The rates of decomposition of the bistriazenes (1) and (2) were measured in buffer at pH 7.4. Bistriazenes 1 had half-lives of approximately 5 hours under those conditions, while bistriazenes 2 were somewhat less stable, having half-lives of about 5 minutes. This is compared to bistriazenes where EG is methyl, which have half-lives on the order of several seconds under these conditions. The nature of the linker had little effect on the decomposition rate.

The enhanced chemical stability of bistriazenes (1) and (2) had little effect on their ability to interact with DNA. This was determined by the reaction of the bistriazenes with the supercoiled plasmid pBR322. For example, the ability of bistriazene (1a) to open, linearize, and finally to shear the plasmid (FIG. 7) was essentially identical to that observed for 1,2-bis(methyltriazeno)ethane (FIG. 6). Thus, electron withdrawing groups EG stabilize bistriazenes with respect to proteolytic decomposition in buffer, while leaving unaffected the DNA-damaging activity.

Furthermore, preliminary cytotoxicity data obtained via the clonogenic assay described above revealed that bistriazenes (1a) and (1b) are potently cytotoxic. These data are shown in Table 1, below.

TABLE 1

Cytotoxicity of bis(3-pyridyltriazeno)ethane(1a) and bis(3-pyridyltriazeno)butane(1b) on Human Tumor Cell Lines

| Drug | Cell Line[a] | Test/Control (%) at Drug Concentration ($\mu$g/ml) | | |
|---|---|---|---|---|
| | | 1.0 | 10.0 | 100.0 |
| 1a | LXFL 529 | 51 | 0+++ | 0+++ |
| | PRCL DU145Y | 84 | 44+ | 0+++ |
| | RXF 1220 | 99 | 74 | 4+++ |
| 1b | LXFL 529 | 71 | 1+++ | 1+++ |
| | PRCL DU145Y | 94 | 62 | 4+++ |
| | RXF 1220 | 82 | 70 | 8+++ |
| DTIC[b] | LXFL 529 | 63 | 35+ | 8+++ |
| | PRCL DU145X | 70 | 44+ | 43+ |
| | RXF 1220 | 54 | 44+ | 24+ |
| CYCM[c] | LXFL 529 | 115 | 94 | 19++ |
| | PRCL DU145X | 108 | 90 | 47+ |
| | RXF 1220 | 67 | 51 | 9+++ |

[a]LXFL 529 is a large cell lung cancer line, PRCL DU145X is a prostate carcinoma, and RXF 1220 is a renal carcinoma.
[b]DTIC (5-(dimethyltriazeno) imidazole-4-carboxamide) is a clinically used drug, and is positive in this panel.
[c]CYCM, 4-hydroperoxycyclophosphamide, is an activated form of the well-known cytotoxic agent cytoxan.

Thus, electron attracting EGs in the bistriazenes encompassed by the present invention impart desirable enhanced chemical stability without affecting the DNA damaging effect of these drugs.

Specifically, the following types of EGs fulfill this requirement:

(a) Phenyl and substituted phenyl groups:
The substituents can include electron attracting moieties such as one or more nitro (—$NO_2$) groups, one or more halogen atoms (such as fluorine, chlorine, bromine, or iodine), one or more cyano (—CN) groups, one or more trifluoromethyl groups, one or more carboxyl groups or various combinations of these substituents.

(b) Arylalkyl or substituted arylalkyl groups:
These include benzyl ($C_6H_5CH_2$) and benzyls substituted as described in (a) above. Also included are condensed ring arylalkyls such as naphthylmethyl.

(c) Heterocyclic ring systems:
These include, but are not limited to, 2-pyridyl, 3-pyridyl and 4-pyridyl, 4-imidazolyl and 4-imidazolyl-5-carboxamide, various EGs derived from pyrimidines (cytosine, thymidine and uracil) and purines (adenine and guanine), and various oligonucleotides derived from combinations of purines and pyrimidines. The oligonucleotides can be held together by normal phosphate links, or by methylphosphonate or phosphorothioate links.

(d) Amine and polyamine-derived EGs:
Since amines can be protonated at physiological pH, and would thus fulfill the same stabilizing role, groups such as 2-aminopropyl, and 2-(N,N-dialkylamino)propyl such as 2-(N,N-dimethylamino)propyl or 2-(N,N-diethylamino) propyl are useful. Also contemplated are groups which have more than one amino group, such as 2-(N-[4-(N'-propylamino)butyl]amino)propyl(—$CH_3CH_2CH_2NH$—$CH_2CH_2CH_2CH_2NHCH_2CH_2CH_2$—). These are analogs to natural polyamines.

As a means of enhancing the reactivity of bistriazenes toward DNA, resulting in drugs that would require administration in lower doses to achieve similar therapeutic results, the present inventors have modified the linker in the bistriazene structure. Specifically, bistriazene (3) was prepared:

$$CH_3—N=N——NH—CH_2CH_2N(CH_3)—CH_2CH_2NH—N=N—CH_3 \quad (3)$$

This compound is at least 100 times more reactive toward pBR322 than 1,2-bis(methyltriazeno)ethane (cf. FIGS. 6 and 8). At the beginning of this application there is discussed a paper by Vaughan et al. (1984) J. Med. Chem. 27:357-63 which describes a bistriazene in which the linker is the same as in bistriazene (3). The Vaughan et al bistriazene is, however, substantially different from (3) for the following reasons:

1. The saturated nitrogens therein have additional substituents (methyl groups). Such bistriazenes would require a double metabolic demethylation in order to become alkylating agents—a very unlikely scenario. In contrast, the bistriazenes of the present invention require H atoms instead of alkyl groups in that position.

2. The synthetic method is very different, as is the chemistry of the Vaughan et al bistriazene, as compared to the bistriazenes of the present invention.

3. The Vaughan et al. bistriazene would be expected to act like a monotriazene in biological systems, i.e., it would be a simple alkylating agent.

Thus, the bistriazenes of the present invention include those with the following linker modifications:

(a) The linker shown in structure (3), together with various modifications of that scheme, i.e., a central nitrogen flanked by $(CH_2)_n$, where n=1–5.

(b) Instead of a methyl on the central nitrogen, the latter can be substituted by hydrogen or other normal alkyl groups from methyl to pentyl.

(c) The linker can also possess more than one nitrogen. Specifically, the following linker, which would closely mimic a polyamine structure, is contemplated:

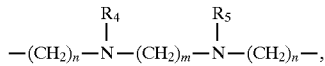

where n=1–5, m=1–5, and $R_4$ and $R_5$=normal alkyl up to pentyl.

(d) Instead of the central atom being N, it can also be oxygen, or sulfur. In those cases, no other substituents on the oxygen atom would be possible, except those forming the linker. In the case of sulfur, however, the atom could be oxidized to the sulfoxide or the sulfone.

PHARMACEUTICAL PREPARATIONS

The bistriazene compounds of the present invention, or physiologically acceptable salts thereof, can be formulated into a pharmaceutical composition comprising an effective anti-cancer amount of the compound and a pharmaceutically acceptable carrier. An effective anti-cancer amount of the pharmaceutical composition will be administered to the subject, human, animal, or mammal, in a manner which inhibits cancer cell growth or replication. The amount of the compound and the specific pharmaceutically acceptable carrier will vary depending upon the host and its condition, the mode of administration, and the type of cancer being treated.

In a particular aspect, the pharmaceutical composition comprises a bistriazene anti-cancer compound or physiologically acceptable salt thereof in effective unit dosage form. As used herein, the term "effective unit dosage" or "effective unit dose" is denoted to mean a predetermined anti-cancer amount sufficient to be effective against the cancer in vivo. Pharmaceutically acceptable carriers are materials useful for the purpose of administering the medicament, which are preferably non-toxic, and may be liquid materials which are otherwise inert and medically acceptable, and are compatible with the active ingredients.

The pharmaceutical compositions of the present invention can also contain an anti-cancer effective amount of at least one conventional alkylating agent, such as chlorambucil, melphalan, uracil, mustard NF, cyclophosphamide, mechlorethamine hydrochloride, carmustine (BCNU), lomustine, dacarbazine (DTIC), thiotepa NF, and busulfan, or combinations thereof. Pharmaceutical compositions of the present invention can also contain, in addition to a bistriazene compound or physiologically acceptable salt thereof, at least one conventional chemotherapeutic agent other than an alkylating agent, as would be apparent to one of ordinary skill in the art of cancer chemotherapy. Also contemplated in the present invention are pharmaceutical compositions containing a bistriazene compound or physiologically acceptable salt thereof, at least one conventional alkylating agent, and at least one conventional chemotherapeutic agent other than an alkylating agent. Pharmaceutical compositions of the present invention can also include those wherein more than one of the bistriazene cmpounds described supra are employed in conjunction with one another, either alone or in combination with at least one conventional alkylating agent and/or at least one conventional chemotherapeutic agent other than an alkylating agent. All pharmaceutical compositions of the present invention can also contain other active ingredients such as antimicrobial agents and other agents such as preservatives, and can be employed in treating cancer in a mammal, including humans.

These pharmaceutical compositions may take the form of a solution, an emulsion, suspension, ointment or cream. They may be administered parenterally, orally or topically, as an aerosol, spray, or drops, said parenteral administration being conducted intraperitoneally, intramuscularly, subcutaneously, intravenously, intraarticularly, intraarterially, or transdermally, depending upon whether the preparation is used to treat internal or external cancers.

The compositions may contain the compound in an amount of from about 0.1% - about 99% by weight of the total composition, preferably about 1 to about 90% by weight of the total composition. For parenteral injection, the bistriazene compound can be dissolved in a pharmaceutically suitable carrier such as purified corn oil, propylene glycol, triolene, or dimethyl sulfoxide, and the dose may be about 0.1 mg to about 1000 mg per kilogram per day. If administered intraperitoneally, the compounds may be dissolved in a suitable vehicle, as above, and the dose may be about 1 mg to about 500 mg per kilogram per day. If injected intramuscularly, the compounds can be dissolved in oil or another compatible vehicle, and the dose can be about 0.1 mg to about 1000 mg per kilogram per day. In any case, injections can be carried out once or several times per day over a five day course depending upon the route of administration and the condition of the patient. After such courses, a recovery period of various length may be necessary. Additional courses may then be required under specific conditions. Total adult doses can range from about 0.1 to about 5000 mg, with dosages in the range of from about 10 to about 1000 mg being preferred. For certain particular applications, oral administration of bistriazenes encapsulated in liposomes or time-release formulations or dispersed in compatible emulsions together with stabilizing and/or dispersing agents may be the method of choice.

For topical application, to treat surface lesions such as basal cell and squamous cell carcinomas or non-metastasized melanomas, as well as certain non-malignant conditions which are characterized by rapid cell proliferation but which may not be amenable to surgical treatment, bistriazenes may be formulated in oil or cream.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. Compounds and physiologically acceptable salts of the formula:

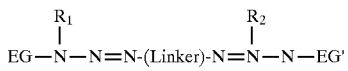

wherein the Linker is selected from the following groups in which n and m are each 1–5; $R_1$ and $R_2$ are each selected from the group consisting of hydrogen, alkyl, substituted alkyl of chain length 1–20, an arylalkyl group, and a substituted arylalkyl group, aryl, a substituted phenyl group, an amine group, and a heterocyclic group; $R_3$ is a hydrogen or a $C_1$–$C_5$ n-alkyl; and $R_4$ and $R_5$ each $=C_1$–$C_5$ n-alkyl; said linker being

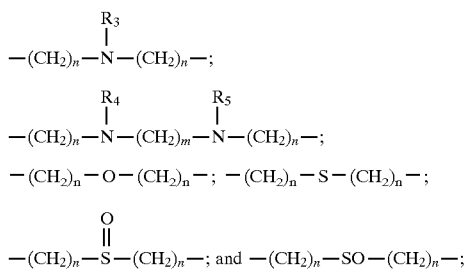

EG and EG' are each selected from the group consisting of a phenyl group, a substituted phenyl group, an arylalkyl group, a substituted arylalkyl group, a heterocyclic group, and an amine group.

2. The compound or physiologically acceptable salt of claim 1, wherein said Linker is

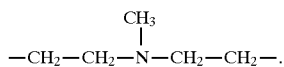

3. The compound or physiologically acceptable salt of claim 1, wherein the substituents of said substituted phenyl group and said substituted arylalkyl group are electron attracting moieties.

4. The compound or physiologically acceptable salt of claim 3, wherein said electron attracting moieties are selected from the group consisting of one or more nitro groups, one or more halogen atoms, one or more cyano groups, one or more trifluoromethyl groups, and one or more carboxyl groups.

5. The compound or physiologically acceptable salt of claim 4, wherein said halogen atoms are selected from the group consisting of fluorine, chlorine, bromine, and iodine.

6. The compound or physiologically acceptable salt of claim 1, wherein said arylalkyl group is a benzyl group.

7. The compound or physiologically acceptable salt of claim 1, wherein said substituted arylalkyl group is a substituted benzyl group.

8. The bistriazene compound or physiologically acceptable salt thereof of claim 1, wherein said arylalkyl group $R_1$ or $R_2$ is a polycyclic arylalkyl group.

9. The compound or physiologically acceptable salt of claim 8, wherein said condensed ring arylalkyl group is a naphthylmethyl group.

10. The compound or physiologically acceptable salt of claim 1, wherein said EG heterocyclic group is selected from the group consisting of a 2-pyridyl group, a 3-pyridyl group, a 4-pyridyl group, a 4-imidazolyl group, a 4-imidazolyl-5-carboxamide group, a pyrimidinyl group, a purinyl group, and a DNA oligomer bonded to said bistriazene compound or physiologically acceptable salt thereof either through the 3' or 5'-position of the terminal deoxyribose ring.

11. The compound or physiologically acceptable salt of claim 10, wherein said DNA oligomer comprises purines and pyrimidines.

12. The compound or physiologically acceptable salt of claim 10, wherein said DNA oligomer is held together by phosphate linkages, methylphosphonate linkages, or phosphorothioate linkages.

13. The compound or physiologically acceptable salt of claim 1, wherein said amine is selected from the group consisting of a 2-aminopropyl group and a 2-(N,N-dialkylamino)propyl group.

14. The compound or physiologically acceptable salt of claim 13, wherein said 2-(N,N-dialkylamino)propyl group is selected from the group consisting of a 2-(N,N-dimethylamino)propyl group and a 2-(N,N-diethylamino) propyl group.

15. The bistriazene compound or physiologically acceptable salt thereof, of claim 1, wherein said amine group is a polyamine.

16. The compound or physiologically acceptable salt of claim 1, wherein said compound or physiologically acceptable salt is Bis((2-(methyltriazeno)ethyl)ethyl)methyl amine.

17. A pharmaceutical composition comprising an anti-cancer effective amount of said bistriazene compound, or physiologically acceptable salt thereof, of claim 1 and a pharmaceutically acceptable carrier.

18. A pharmaceutical composition comprising an anti-cancer effective amount of at least one bistriazene compound, or physiologically acceptable salt thereof, of claim 16 and a pharmaceutically acceptable carrier.

19. The pharmaceutical composition of claim 17, comprising an anti-cancer effective amount of said bistriazene compound and an anti-cancer effective amount of a compound selected from the group consisting of bis(2-chloroethyl)nitrosourea, mitomycin, cyclophosphamide, ifosphamide, or any other conventional chemotherapeutic alkylating agent.

20. A pharmaceutical composition, comprising an anti-cancer effective amount of at least one bistriazene compound or physiologically acceptable salt thereof, of claim 16, and at least one of an anti-cancer effective amount of an alkylating agent selected from the group consisting of bis(2-chloroethyl)nitrosourea, mitomycin, cyclophosphamide, ifosphamide, or any other conventional chemotherapeutic alkylating agent, and a conventional chemotherapeutic agent other than an alkylating agent.

21. The bistriazene compound or physiologically acceptable salt thereof, of claim 1, wherein said arylalkyl group or substituted arylalkyl group is a condensed ring arylalkyl group.

22. The compound or physiologically acceptable salt of claim 15, wherein said polyamine is 2-(N-[4-(N'-propylamino)butyl]amino)propyl ($CH_3CH_2CH_2NH$—$CH_2CH_2CH_2CH_2NH$—$CH_2CH_2CH_2$—).

23. The bistriazene compound or physiologically acceptable salt thereof of claim 1 wherein said heterocyclic group $R_1$ or $R_2$ is a heterocyclic group of 2–40 non-hydrogen atoms, containing 1–6 rings.

24. A compound or a physiologically acceptable salt thereof, which is selected from the group consisting of:

1,4-Bis(benzyltriazeno)ethane,
1,2-Bis(benzyltriazeno)ethane,
1,4-Bis(2-pyridyltriazeno)ethane,
1,2-Bis(2-pyridyltriazeno)ethane,
1,4-Bis(3-pyridyltriazeno)ethane, and
1,2-Bis(3-pyridyltriazeno)ethane.

* * * * *

UNITED STATES PATENT AND TRADEMARK OFFICE
CERTIFICATE OF CORRECTION

PATENT NO. : 5,808,038
DATED : September 15, 1998
INVENTOR(S) : Christopher A. Michejda et al.

It is certified that error appears in the above-identified patent and that said Letters Patent is hereby corrected as shown below:

Column 22,
Lines 45-46, please replace "2-(N-[4-(N'-propylamino)butyl]amino)propyl" with
-- 3-(N-[4-(N'-propylamino)butyl]amino)propyl. --.

Signed and Sealed this

Sixth Day of September, 2005

JON W. DUDAS
*Director of the United States Patent and Trademark Office*